United States Patent [19]

Brewester et al.

[11] 4,247,486
[45] Jan. 27, 1981

[54] CYCLIC HYDROFORMYLATION PROCESS

[75] Inventors: Everard A. V. Brewester, Reading, England; Roy L. Pruett, Charleston, W. Va.

[73] Assignee: Union Carbide Corporation, New York, N.Y.

[21] Appl. No.: 776,934

[22] Filed: Mar. 11, 1977

Related U.S. Application Data

[63] Continuation-in-part of Ser. No. 674,823, Apr. 8, 1976.

[51] Int. Cl.³ .................. C07C 45/50; C07C 47/02
[52] U.S. Cl. .................................................. 568/454
[58] Field of Search ........................... 260/604 HF

[56] References Cited

U.S. PATENT DOCUMENTS 3,239,566  3/1966  Slaugh .......................... 260/604 HF

FOREIGN PATENT DOCUMENTS

1228201  4/1971  United Kingdom ............. 260/604 HF
1387657  3/1975  United Kingdom ............. 260/604 HF

*Primary Examiner*—Werren B. Lone
*Attorney, Agent, or Firm*—Reynold J. Finnegan

[57] ABSTRACT

Hydroformylating alpha-olefins in a cyclic homogeneous liquid phase process utilizing a modified rhodium catalyst, the improvement which involves utilizing a gas recycle to maintain the liquid level in the reaction and control build-up of high molecular weight components.

10 Claims, 1 Drawing Figure

CYCLIC HYDROFORMYLATION PROCESS

This application is a continuation-in-part of copending U.S. Application Ser. No. 674,823, filed Apr. 8, 1976, now abandoned.

This invention relates to the preparation of aldehydes by the "Hydroformylation" process in which an alpha-olefin is hydroformylated with carbon monoxide and hydrogen in the presence of a rhodium catalyst.

J. Falbe, "Carbon Monoxide in Organic Synthesis", Springer-Verlag, New York (1970), at page 3, has stated: "Hydroformylation is the reaction of an unsaturated compound (or a saturated compound which may generate an unsaturated compound) with carbon monoxide and hydrogen to yield an aldehyde". The process has also been called the Oxo process. Until recently, all commercial hydroformylation reactions were catalyzed by cobalt carbonyl catalysts. According to Falbe (at page 70), supra, with the single exception of the process developed by Shell, "all industrially applied oxo processes more or less follow the technique which was developed by Ruhrchemie AG in Oberhausen/Germany in co-operation with BASF". He states that the existing oxo plants operate continuously and, in general, "they consist of the following sections: 1. Hydroformylation reactor. 2. Catalyst removal section. 3. Catalyst work-up and make-up section. 4. Aldehyde distillation. 5. Aldehyde hydrogenation reactor. 6. Alcohol distillation".

The Shell process differs by employing a modified cobalt catalyst made by combining in the hydroformylation reactor a cobalt salt of organic acids, trialkyl phosphines (e.g. tributyl phosphine) and alkali, such as KOH. The in situ formed $HCo(CO)_3PR_3$ catalyst "is thermally more stable than $HCo(CO)_4$" thus allowing lower reactor pressure of "around 100 atm, versus 200-300 atm in the other processes" (Falbe, supra, page 73).

Though the earliest Oxo plants were intended to be a heterogenous reaction patterned after Fischer-Tropsch catalysis, it was eventually found that the catalysis was homogeneous (Falbe, supra, page 14). The separation and recovery of the catalyst was therefore an essential step in the Oxo process. This is significantly the case when the catalyst comprises the precious metal rhodium. As stated by Cornils et al., "Hydrocarbon Processing", June 1975, at page 86: "While Rh compounds are more active than cobalt, they are much more expensive. Cobalt costs approximately 20 DM/kg and rhodium between 44,000 and 72,000 DM/kg (September 1974 and February 1975). This shows the speculative character of the rhodium price. Cost would be of no importance if rhodium could be 100 percent recovered and used at low metal concentration levels. Impossible economic rhodium recycle has avoided application of unmodified Rh compounds so far, even when branched chain aldehydes are desired or when only Rh salts can enable the oxo reaction. This is because the low Rh concentrations desired—from several ppm* up to several hundred ppm, related to olefin feed (cobalt 0.1 up to 1 percent, depending on the process applied)—make even more difficult a chemical, thermal or extractive treatment of the metal carbonyl containing oxo products. Therefore there are a number of special processes for the removal of rhodium traces from oxo products (e.g. adsorption on solids with large surface, distillative concentration with the heavy ends of oxo synthesis, the treatment with steam, halogens or carboxylic acids or others). Often these methods require an expensive recovery step for concentration outside of the oxo unit. A rhodium loss of only one ppm per kilogram of oxo product produced causes material costs of approximately 0.04 up to 0.07 DM/kg "(compared to 0.01 DM/kg with Co catalysts)."

*"ppm" means parts per million)

Cornils et al., pages 87, 88 and 90, depict in FIG. 9 a proposed commercial plant design based upon a modified rhodium catalyzed Oxo process. They characterize that the catalyst has to be recycled to the reactor from the distillation column. Owing to the formation of heavy ends, Cornils et al., at page 88, state that "a complete recycling of rhodium only via the 'primary' recycle 9* would cause enrichment of higher boiling components". According to Cornils et al., page 88, "to avoid this, part of the bottom of column 3* is withdrawn continuously as a slipstream and distilled in column 6* to give a 'light aldols' overhead". They continue with the following:

"Provided there is sufficient activity, the bottoms which are thermally treated twice at this point are recycled to the reactor as a 'secondary' Rh cycle 10*. The distillation in column 6* does not remove the medium and high boiling byproducts of oxo synthesis, the latter because they can not be separated from the excess ligand. The separation of the Rh complexes from the medium boiling components is done in column 7* which is fed a slipstream of the bottoms of 6*. The bottoms of 7* are treated thermally so often that their rhodium content is oxo inactive and must be worked-up in an external make-up step 8*. This rhodium is recycled to the reactor as a 'tertiary' Rh recycle 11*, losing however the complex bonded ligand and the excess of complexing ligands. The amount per year of rhodium passing the tertiary recycle is about twice the first Rh filling of the whole oxo system."

Cornils et al. state at page 89:

"Rhodium concentrations of 0.1 percent together with the amounts of rhodium being present in the different steps of recycle and recovery at each moment require high cost for the first catalyst investment. The relation of the first catalyst investment in cobalt and in Rh modified oxo units is 1:5 (1:3, depending on Rh price). More important than the first catalyst investment are the rhodium leakage and working losses. In comparison to other commercial processes using noble metal catalysts, a rhodium loss of one milligram per kilogram of oxo products is regarded to be realistic. This results in material costs of approximately 0.04–0.07 DM/kg, depending on the Rh price. To equal the material cost of the conventional oxo process catalyst the rhodium losses have to decrease to less than 0.3 ppm."

A similar process to that described by Cornils et al. is set forth in British Pat. No. 1,228,201. In the processes described in that patent, the catalyst recycle is a critical facet of the process except in those cases where the catalyst is on a solid support in a fixed bed system. However, as was pointed out previously by J. Falbe, the reaction is in reality a homogeneous reaction and one would have to presume substantial catalyst losses by putting the rhodium on a inert support.

In British Pat. No. 1,312,076, there is employed a different technique for separation of the catalyst from the product of the reaction. This involves removing a *vapor* product stream overhead from which the aldehyde product is separated by fractional distillation, continuously withdrawing from the reactor a *liquid* stream comprising the catalyst catalyst, aldehyde and high boiling residues, passing the liquid stream under reaction pressure over the surface of a membrane such that a proportion of the high boiling residues and aldehydes permeate through the membrane and are removed, with recycling of the remainder of the liquid stream containing the catalyst to the reactor.

In British Provisional Specification No. 23678/69, there is noted the fact that in homogeneous catalysis of the type described herein, the removal of catalyst from the reaction products for recycle is a difficult operation. It is stated in the Specification that the catalyst can be recycled in the heavy residue obtained after distillation of the main reaction products at the expense of catalyst loss.

To further demonstrate the difficulties associated with recovering catalyst from the oxo reaction, reference is made to Olivier and Snyder, U.S. Pat. No. 3,539,634, patented Nov. 10, 1970, which describes passing the heavy and/or bottoms of the separated products of the reaction containing the catalyst through an inert bed from which is extracted the catalyst with reaction solvent. Such a process demands that the solvent be a type which has extraction capabilities while at the same time requires infinite extraction capabilities to insure no catalyst loss.

There is described herein a process for the manufacture of such Oxo products by hydroformylation of alpha-olefins with a modified rhodium catalyst which avoids for all practical purposes rhodium catalyst losses over extended periods of time.

The process of this invention is a continuous one for producing aldehydes by the hydroformylation of alpha-olefins containing two to about five carbon atoms. It involves establishing a liquid body of a homogeneous mixture containing the olefin, carbon monoxide and hydrogen being supplied thereto, aldehyde products and higher boiling aldehyde condensation products being continuously formed therein, a soluble rhodium catalyst complexed with carbon monoxide and a triaryl phosphine. The amount of triaryl phosphine provided in the liquid body is equal to at least 10 moles for each mol of rhodium metal provided in the liquid body. There is supplied to the liquid body a gaseous recycle stream comprising hydrogen and olefin and there is supplied make-up quantities of carbon monoxide, hydrogen and olefin to the liquid body. The temperature of the liquid body is maintained at about 50° C. to about 130° C., and the total pressure is maintained at less than about 400 pounds per square inch absolute. The carbon monoxide partial pressure in the reaction is less than about 50 pounds per square inch absolute and the hydrogen partial pressure is less than about 200 pounds per square inch absolute. There is removed from the liquid body a vaporous mixture comprising olefin, hydrogen, vaporized aldehyde products and an amount of vaporized aldehyde condensation products essentially equal to the rate of their formation in the body whereby the size of the liquid body is maintained at a predetermined value. Aldehyde products and aldehyde condensation products are recovered from the vaporous mixture and this forms the gaseous recycled stream which is supplied to the liquid body as mentioned above.

U.S. Pat. No. 3,527,809, entitled "Hydroformylation Process" by R. L. Pruett and J. A. Smith, issued Sept. 8, 1970, discloses a significant development in hydroformylation of alpha-olefins to produce aldehydes at high yields, low temperatures and pressures, excellent catalyst stability and which when the alpha-olefin contains 3 or more carbon atoms, produces aldehyde mixtures containing a high normal to iso- (or branched-chain) isomer ratio. The process employs certain rhodium complex compounds to effectively catalyze under a defined set of variables, in the presence of select triorganophosphorus ligands, the hydroformylation of olefins with hydrogen and carbon monoxide. The variables include (1) the rhodium complex catalyst, (2) the olefin feed, (3) the triorganophosphorus ligand and its concentration, (4) a relatively low temperature range, (5) a relatively low total hydrogen and carbon monoxide pressure, and (6) a limitation on the partial pressure exerted by carbon monoxide. The process of this invention adopts the variables of the invention of U.S. Pat. No. 3,527,809, and by experiences from operations herein described establishes the tremendous advance that invention represents in the Oxo art.

Among the catalysts described in the aforesaid U.S. patent, are compounds containing rhodium in complex combination with the carbon monoxide and triarylphosphorus ligands in particular triarylphosphine ligands exemplified by triphenylphosphine (TPP). A typical active catalytic species is rhodium hydridocarbonyltris (triphenylphosphine) which has the formula $RhH(CO)[P(C_6H_5)_3]_3$. The process uses an excess of the triorganophosphorus ligand.

The active rhodium catalyst, as is known in recent literature, can be preformed and then introduced into the reaction mixture media, or the active catalyst species can be prepared in situ during the hydroformylation reaction. As an example of the latter, (2,4-pentanedionato) dicarbonylrhodium(I) can be introduced into the reaction medium where, under the operative conditions therein, it reacts with the triorganophosphorus ligand, e.g., triphenylphosphine, to thus form active catalyst such as rhodium hydridocarbonyl-tris(triphenylphosphine).

When the process of U.S. Pat. No. 3,527,809 employs normally-liquid inert organic solvents which are not products of the reaction or reactants in the process the product mixture eventually becomes, either at room temperature or at the chosen operating temperature of, for example, 80° C., slightly cloudy in nature or it possesses a noticeable precipitation. Elemental analyses indicates that such solids (cloudiness or precipitate) contain rhodium. In some instances, it appears that "polymeric" rhodium complex solids have formed and in other instances, the solids are similar to an active form of the rhodium complex species. Such solids can become lost in the system, e.g., deposit in small crevices or plug valves. As noted above, a truly effective commercial Oxo operation cannot tolerate the loss of even small quantities of rhodium. A further disadvantage of introducing the rhodium species as a solution in such an extraneous organic liquid is the obvious requirement of separating the oxygenated products formed in the reaction from such organic liquid. Since Oxo reactions produce aldehydes and high boiling aldehyde condensation products which are removed to maintain the solvent concentrations, as noted above, the removal of the condensation products by distillation affects the solvent, some being distilled (if not all distilled), and the Rh values it contains. The initial introduction into the Oxo reaction zone of a catalytic solution in extraneous organic liquids is effective. However, such a commercially based Oxo operation demands continuous or intermittent catalyst introduction which can be fresh catalyst, regenerated catalyst, or catalyst contained in a recycle stream. Catalyst losses are the result of such practices.

U.S. Pat. No. 4,148,830 and British Patent Specification No. 1,338,237, employ the high boiling liquid aldehyde condensation products as a primary solvent for the catalyst. As a result, no removal of the solvent from the catalyst is necessary except for a small purge stream to keep down the concentration of condensation products and poisons to the reaction. As a result, the hydroformylation of 3 carbon olefins, or higher, maintains the high ratio of normal/iso isomer distribution of aldehydic product over extended periods of time and the continuous recycling of the rhodium species in substantial quantities of such condensation products does not result in extensive precipitation of the rhodium in one form or another. No discernible loss in the life of the catalyst was detected over extended periods of operation. The use of such condensation products as the media to solubilize the rhodium-containing catalyst was advantageous from the standpoint that extraneous organic liquids could be excluded entirely from the hydroformylation zone, if desired. The use of excess, free triorganophosphorus ligand in the reaction medium containing the dissimilar high boiling condensation products to provide the advantages cited in U.S. Pat. No. 3,527,809 did not exhibit the activity or solubility of the rhodium complex catalyst even over long periods of continuous operation. Since these condensation products are formed in situ, the economics of the aforementioned process are extremely favorable.

After substantial repeated use it was found that continuous recycle of rhodium species dissolved in the high boiling liquid condensation products presented disadvantages. The constant movement of catalyst led to some catalyst loss; considerable catalyst volume was required because in the liquid recycle a portion of the catalyst is outside of the reactor; rate of residue formation remained at significant levels and had to be removed, thus affecting catalyst stability on such occasions; control of carbon monoxide gas pressure was difficult; the nature of the recycle brought about heat losses because of the constant movement of hot liquids through the system; and there developed a tendency to have small oxygen leakage which proved deleterious to the process.

It has been determined that a hydroformylation reaction using a non-volatile catalyst, such as hydridocarbonyltris (triphenylphosphine)rhodium(I), in the liquid phase can be carried out in a more convenient manner and with simpler equipment by allowing the aldehyde reaction product and their higher boiling condensation products to distil out of the catalyst containing liquid body (or solution) at the reaction temperature and pressure, by condensing the aldehyde reaction product and the condensation products out of the off gas from the reaction vessel in a product recovery zone and by recycling the unreacted starting materials (e.g., carbon monoxide, hydrogen and/or alpha-olefin) in the vapor phase from the product recovery zone to the reaction zone. Furthermore, by recycling gas from the product recovery zone coupled with make-up starting materials to the reaction zone in sufficient amounts, it is possible, using a $C_2$ to $C_5$ olefin as the alpha-olefin starting material, to achieve a mass balance in the liquid body in the reactor and thereby remove from the reaction zone at a rate at least as great as their rate of formation essentially all the higher boiling condensation products resulting from self condensation of the aldehyde product. If the gas recycle is not sufficient, such condensation products would otherwise build up in the reaction vessel.

According to the present invention a process for the production of an aliphatic aldehyde containing from 3 to 6 carbon atoms comprises passing an aliphatic alpha-olefin containing from 2 to 5 carbon atoms together with hydrogen and carbon monoxide at a prescribed temperature and pressure through a reaction zone containing the catalyst dissolved in the liquid body, the catalyst being essentially non-volatile and being effective for hydroformylation of the alpha-olefin, continuously removing a vapor phase from the reaction zone, passing the vapor phase to a product separation zone, separating a liquid aldehyde containing product in the product separation zone by condensation from the gaseous unreacted starting materials, and recycling the gaseous unreacted starting materials from the product separation zone to the reaction zone. Preferably the gaseous unreacted starting materials plus make-up starting materials are recycled at a rate at least as great as that required to maintain a mass balance in the reaction zone.

In the process of the invention there is contemplated the use of alpha-olefins of 2 to 5 carbon atoms, preferably 2, 3 or 4 carbon atoms. Such alpha-olefins are characterized by a terminal ethylenic carbon-to-carbon bond which may be a vinylidene group, i.e., $CH_2=C<$, or a vinyl group, i.e., $CH_2=CH—$. They may be straight-chain or branched-chain and may contain groups of substituents which do not essentially interefere with the course of this process. Illustrative alpha-olefins include ethylene, propylene, 1-butene, iso-butylene, 2-methyl-1-butene, 1-pentene, and the like.

The reaction is advantageously conducted at a temperature of from about 50° C. to about 140° C. A temperature in the range of from about 60° C. to about 120° C. is preferred and it will usually be convenient to operate at a temperature of from about 90° to about 115° C.

A feature of the invention is the low total pressures which are required to effect a commercial process. Total pressures less than about 400 psia and as low as one atmosphere, and lower, can be employed with effective results. Total pressures of less than 350 psia are preferred. The reaction can be effected at pressures ranging between about 100 to about 300 psia.

The partial pressure of the carbon monoxide is an important factor in the process of the invention. It has been observed that when using the complex rhodium catalysts a noticeable decrease in the normal/iso aldehydric product isomer ratio occurs as the partial pressure attributable to carbon monoxide approaches a value of about 75 percent of the total gas pressure $(CO+H_2)$. In general, a partial pressure attributable to hydrogen of from 25 to 95 percent and more, based on the total gas pressure $(CO+H_2)$ is suitable. It is generally advantageous to employ a total gas pressure in which the partial pressure attributable to hydrogen is significantly greater than the partial pressure attributable to carbon monoxide, e.g., the hydrogen to carbon monoxide ratio being between 3:2 and 100:1. Routinely, this ratio can be about 62.5:1 to about 12.5:1.

The partial pressure of the α-olefin in the reaction zone may be up to about 35 percent of the total pressure, preferably in the region of 10 to 20 percent of the total pressure.

In a preferred operation the CO partial pressure is typically not in excess of about 50 p.s.i.a., most desirably not in excess of about 35 p.s.i.a. The preferred hydrogen partial pressure should be less than about 200 p.s.i.a. For example, the $H_2$ partial pressure may be 125 p.s.i.a. and the CO partial pressure may range from 2 to 10 p.s.i.a.

The catalyst may be any non-volatile catalyst that is effective for hydroformylation of alpha-olefins but in view of the known advantages as taught in U.S. Pat. No. 3,527,809 of catalysts based on rhodium, it constitutes in modified form the catalyst of choice. When a $C_3$ or higher olefin is used as a starting material it is preferred to choose a catalyst that gives a high n-/iso-ratio in the aldehyde product mixture. The general class of rhodium catalysts depicted in U.S. Pat. No. 3,527,809 may be used in the practice of this invention.

The preferred catalyst of this invention comprises rhodium complexed with carbon monoxide and a triarylphosphine ligand. The most desirable catalyst is free of halogen such as chlorine, and contains hydrogen, carbon monoxide and triaryl phosphine complexed with rhodium metal to produce a catalyst soluble in the aforementioned liquid body and stable under the conditions of the reaction. Illustrative triarylphosphine ligands are triphenylphosphine, trinaphthylphine, tritolylphosphine, tri(p-biphenyl)phosphine, tri(p-methoxyphenyl)phosphine, tri(m-chlorophenyl)-phosphine, p-N,N-dimethylaminophenyl bis-phenyl phosphine, and the like. Triphenylphosphine is the preferred ligand. As pointed out previously, the reaction is effected in a liquid body containing excess, free triarylphosphine.

Rhodium is preferably introduced into the liquid body as a preformed catalyst, e.g., a stable crystalline solid, rhodium hydridocarbonyl-tris(triphenyl phosphine), $RhH(CO)(PPh_3)_3$. The rhodium can be introduced to the liquid body as a precursor form which is converted in situ into the catalyst. Examples of such precursor form are rhodium carbonyl triphenylphosphine acetylacetonate, $Rh_2O_3$, $Rh_4(CO)_{12}$, $Rh_6(CO)_{16}$, and rhodium dicarbonyl acetylacetonate. Both the catalyst compounds which will provide active species in the reaction medium and their preparation are known by the art, see Brown et al., *Journal of the Chemical Society*, 1970, pp. 2753–2764.

In ultimate terms the rhodium concentration in the liquid body can range from about 25 ppm to about 1200 ppm of rhodium calculated as free metal, and the triarylphosphine is present in the range of about 0.5 percent to about 30 percent by weight, based on the weight of the total reaction mixture, and in an amount sufficient to provide at least 10 moles of free triarylphosphine per mole of rhodium.

The significance of free ligand is taught in U.S. Pat. No. 3,527,809, supra, British Pat. No. 1,338,225, and Brown et al., supra, pages 2759 and 2761.

In general the optimum catalyst concentration depends on the concentration of the alpha-olefin, such as propylene. For example, the higher the propylene concentration the lower usually will be the catalyst concentration that can be used to achieve a given conversion rate to aldehyde products in a given size of reactor. Recognizing that partial pressures and concentration are related, the use of higher propylene partial pressure leads to an increased proportion of propylene in the "off gas" from the liquid body. Since it may be necessary to purge part of the gas stream from the product recovery zone before recycle to the liquid body in order to remove a portion of the propane which may be present, the higher the propylene content of the "off gas" is, the more propylene that will be lost in the propane purge stream. Thus it is necessary to balance the economic value of the propylene lost in the propane purge stream against the capital savings associated with lower catalyst concentration.

An unforeseen advantage of this modified Rh catalyzed process is that in the hydroformylation of ethylene no diethyl ketone is formed in measurable quantities whereas all of the Co catalyzed processes produce significant amounts of diethyl ketone.

It is referred to effect the process of the invention using a liquid phase in the reaction zone which contains one of the aforementioned rhodium complex catalysts and, as a solvent therefor, higher boiling liquid aldehyde condensation products (as hereinafter defined which are rich in hydroxylic commands).

By the term "higher boiling liquid aldehyde condensation products" as used herein is meant the complex mixture of high boiling liquid products which result from the condensation reactions of the $C_3$ to $C_6$ alkanal product of the process of the invention, as illustrated below in the series of equations involving n-butyraldehyde as the model. Such condensation products can be performed or produced in situ in the Oxo process. The rhodium complex species is soluble in these relatively high boiling liquid aldehyde condensation products while exhibiting high catalyst life over extended periods of continuous hydroformylation.

Initially, the hydroformylation reaction can be effected in the absence or in the presence of small amounts of higher boiling liquid aldehyde condensation products as a solvent for the rhodium complex, or the reaction can be conducted with up to about 70 weight percent, and even as much as about 90 weight percent, and more, of such condensation products, based on the weight of the liquid body. A small amount of the higher boiling liquid aldehyde condensation products an be as little as 5 weight percent, preferably more than 15 weight percent, based on the weight of the liquid body.

In the hydroformylation of, for example, propylene, two products are possible, namely normal and iso-butyraldehydes. Since normal butyraldehyde is the more attractive product commercially, high normal/iso ratios of butyraldehydes are desirable. However, the aldehydic products being reactive compounds themselves slowly undergo condensation reactions, even in the absence of catalysts and at comparatively low temperatures, to form high boiling liquid condensation products. Some aldehyde product, therefore, is involved in various reactions as depicted below using n-butyraldehyde as an illustration:

substituted acrolein (II)

(trimer III)      (trimer IV)

(dimer V)      (tetramer VI)

In addition, aldol I can undergo the following reaction:

2 aldol I ⟶ CH₃CH₂CH₂CHCHCH₂CH₃ with OH, and COOCH₂CHCHCH₂CH₂CH₃, CH₂CH₃

(tetramer VII)

The names in parentheses in the afore-illustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self condensation of iso-butyraldehyde and a further range of compounds is formed by condensation of one molecule of normal butyraldehyde with one molecule of iso-butyraldehyde. Since a molecule of normal butyraldehyde can aldolize by reaction with a molecule of iso-butyraldehyde in two different ways to form two different aldols VIII and IX, a total of four possible aldols can be produced by condensation reactions of a normal/iso mixture of butyraldehydes.

Aldol I can undergo further condensation with isobutyraldehyde to form a trimer isomeric with trimer III and aldols VIII and IX and the corresponding aldol X produced by self condensation of two molecules of isobutyraldehyde can undergo further reactions with either normal or isobutyraldehyde to form corresponding isomeric trimers. These trimers can react further analogously to trimer III so that a complex mixture of condensation products is formed.

It is highly desirable to maintain the substituted acrolein II and its isomers at low concentrations, e.g. below about 5 weight percent. The substituted acrolein II, specifically termed 2-ethyl, 3-propylacrolein ("EPA"), is formed in situ along with other condensation products and has been found to inhibit catalyst activity. The ultimate effect of EPA or like products is to reduce hydroformylation rates to such an extent that any process where the EPA is present in amounts greater than about 5 weight percent, even greater than about one percent by weight based on the weight of the liquid body, will suffer an economic penalty.

In a preferred form of the process of the invention the higher boiling liquid condensation products to be used as solvents are preformed prior to introduction into the reaction zone and the start-up of the process. Alternatively, it is possible to add, for example, Aldol I at process start-up and to allow the other products to build up as the reaction proceeds.

In certain instances, it may also be desirable to use minor amounts of an organic co-solvent which is normally liquid and inert during the hydroformylation process, e.g. toluene or cyclohexanone, particularly at start up of the process. They can be allowed to be replaced in the liquid phase in the reaction zone by the higher boiling liquid aldehyde condensation products as the reaction proceeds.

The liquid body will contain, in addition to the catalyst and any added diluent such as free ligand triphenylphosphine, an aldehyde or a mixture of aldehydes and the aldols, trimers, diesters, etc. derived from them.

The relative proportion of each product in solution is controlled by the (amount of gas) passing through the solution. Increasing this amount decreases the equilibrium aldehyde concentration and increases the rate of by-product removal from solution. The by-products include the higher boiling liquid aldehyde condensation products. The decreased aldehyde concentration leads to a reduction in the rate of formation of the by-products.

The dual effect of increased removal rate and decreased formation rate means that the mass balance in by-products in the reactor is very sensitive to the amount of gas passing through the liquid body. The gas cycle typically includes make-up quantities of hydrogen, carbon monoxide and alpha-olefin. However, the most meaningful factor is the amount of recycle gas returned to the liquid body since this determines the degree of reaction, the amount of product formed and the amount of by-product (as a consequence) removed.

Operation of the hydroformylation reaction with a given flow rate of olefin and synthesis gas and with a total low amount of gas recycle less than a critical threshold rate results in a high equilibrium aldehyde concentration in solution and hence, in high by-product formation rates. The rate of removal of by-products in the vapor phase effluent from the reaction zone (liquid body) under such conditions will be low because the low vapor phase effluent flow rate from the reaction zone can only result in a relatively low rate of carry-over of by-products. The net effect is a build-up of by-products in the liquid body solution causing an increase in the solution volume with a consequent loss of catalyst productivity. A purge must therefore be taken from the solution when the hydroformylation process is operated under such low gas flow rate conditions in order to remove by-products and hence maintain a mass balance over the reaction zone.

If however, the gas flow rate through the reaction zone is increased by increasing the gas recycle rate the solution aldehyde content falls, the by-product formation rate is decreased and by-product removal rate in the vapor phase effluent from the reaction zone is increased. The net effect of this change is to increase the proportion of the by-products removed with vapor phase effluent from the reaction zone. Increasing the gas flow rate through the reaction zone still further by a further increase in the gas recycle rate leads to a situation in which by-products are removed in the vapor phase effluent from the reaction zone at the same rate as they are formed, thus establishing a mass balance over the reaction zone. This is the critical threshold gas recycle rate which is the preferred minimum gas recycle rate used in the process of the invention. If the process is operated with a gas recycle rate higher than this threshold gas recycle rate the volume of the liquid body in the reaction zone will tend to decrease and so, at gas recycle rates above the threshold rate, some of the crude aldehyde by-product mixture should be returned to the reaction zone from the product separation zone in order to keep constant the volume of the liquid phase in the reaction zone.

The critical threshold gas recycle flow rate can be found by a process of trial and error for a given olefin and synthesis gas (the mixture of CO and hydrogen) feed rate. Operating at recycle rates below the critical threshold rates will increase the volume of the liquid phase with time. Operating the threshold rate keeps the volume constant. Operating above the threshold rate decreases the volume. The critical threshold gas recycle rate can be calculated from the vapor pressures at the reaction temperature of the aldehyde or aldehydes and of each of the by-products present.

With the process operating at a gas recycle rate at or greater than the threshold rate, by-products are removed in the gaseous vapors removed from the reaction zone containing the liquid body at the same rate as or faster than they are formed, and thus do not accumulate in the liquid phase in the reaction zone. Under such circumstances, it is unnecessary to purge the liquid body containing the catalyst from the reaction zone in order to remove by-products. This has the advantage of obviating removal of catalyst from the reaction zone, except at extended intervals when renovation of the catalyst is necessary, and thus the chance of losses of expensive catalyst by accidental spillage or leakage is reduced. Furthermore there is no need for high temperature treatment of the catalyst-containing purge solution for by-product removal and thus catalyst life is extended. Experience to data suggests that catalyst renovation of any kind is not required for at least one (1) year's operation.

The residence period of aldehyde in the reaction zone can vary from about a couple of minutes to several hours in duration and, as is well appreciated, this variable will be influenced, to a certain extent, by the reaction temperature, the choice of the alpha-olefin of the catalyst, and of the ligand, the concentration of the ligand, the total synthesis gas pressure and the partial pressure exerted by its components, and other factors. As a practical matter the reaction is effected for a period of time which is sufficient to hydroformylate the alpha or terminal ethylenic bond of the alpha-olefin.

A by-product of the hydroformylation process is the alkane formed by hydrogenation of the alpha olefin. Thus, for example, in the hydroformylation of propylene a by-product is propane. Preferably, therefore, a purge stream is taken from the gas recycle stream from the product recovery zone in order to remove propane and prevent its build-up within the reaction system. This purge stream will contain, in addition to unwanted propane, unreacted propylene, some inert gases introduced in the feedback and a mixture of carbon monoxide and hydrogen. The purge stream can, if desired, be submitted to conventional gas separation techniques, e.g. cryogenic techniques, in order to recover the propylene. However, it will usually be uneconomical to do this and the purge stream is typically used as a fuel. The principal composition of the recycle gas are hydrogen and propylene. However, if the CO is not consumed in the reaction, the excess CO will also be part of the recycle gas. Usually the recycle gas will contain alkane even with purging before recycle.

It will be appreciated that the process of the invention can be operated continuously for long periods of time without removing any of the catalyst containing liquid body from the reaction zone. However, from time to time it may be necessary to regenerate the rhodium catalyst, in which case a purge stream can be taken from the reactor through a normally locked valve, fresh catalyst being added to maintain the catalyst concentration in the liquid body or the removed catalyst can be regenerated. After removal from the liquid body in a reactor, the vapor effluent is fed to a product separation zone where the mixture of the aldehyde or aldehydes and the dimers, trimers and other higher boiling liquid condensation products are worked up by conventional techniques, e.g. distillation, in order to remove the aldehyde or aldehydes and, if appropriate, to separate the aldehydes one from another and recover the higher boiling liquid aldehyde condensation products.

The alpha-olefin used as starting material in the process must be rigorously purified in order to remove the typical potential Oxo catalyst poisons, see Falbe, supra, pages 18–22. The carbon monoxide and hydrogen required for the process can be produced by partial oxidation of a suitable hydrocarbon feedstock, e.g. naphtha, and must also be purified rigorously to exclude potential catalyst poisoning impurities.

The invention is further illustrated with reference to the accompanying drawing which schematically shows a diagramatic flowsheet suitable in practising the process of the invention.

Figure 1:
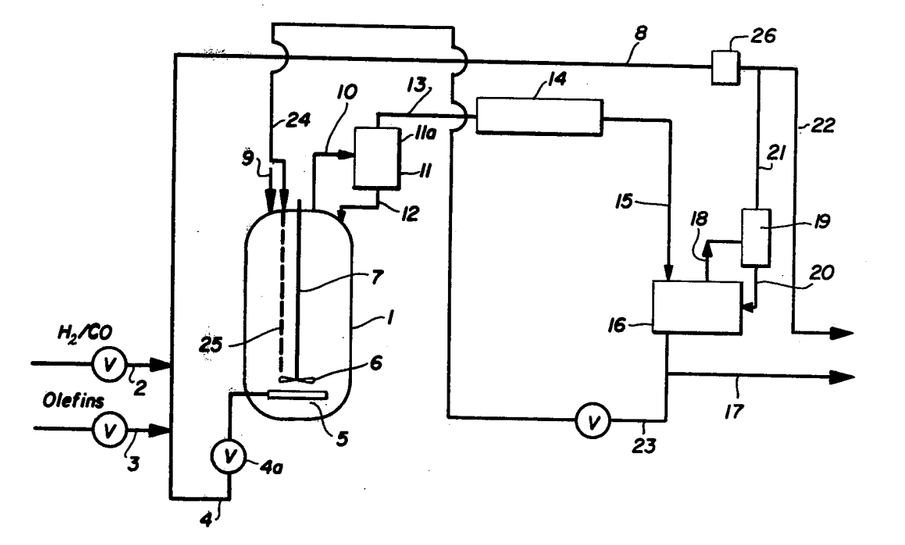

Referring to the drawing, a stainless steel reactor 1 is provided with one or more disc impeller 6 containing perpendicularly mounted blades and rotated by means of shaft 7, by a suitable motor (not shown). Located below the impeller 6 is a circular tubular sparger 5 for feeding the α-olefin, and synthesis gas plug the recycle gas. The sparger 5 contains a plurality of holes of sufficient size to provide sufficient gas flow into the liquid body at about the impeller 6 to provide the desired amount of the reactants in the liquid body. The reactor is also provided with a steam jacket (not shown) by means of which the contents of the vessel can be brought up to reaction temperature at start-up and internal cooling coils (not shown).

Vaporous product effluent from the reactor 1 are removed via line 10 to separator 11 where they are passed through a demisting pad 11a therein to return some aldehyde and condensation product and to prevent potential carry-over of catalyst. The reactor effluent is passed by line 13 to a condenser 14 and then through line 15 to catchpot 16 in which the aldehyde product and any by-product can be condensed out of the off gases (effluent). Condensed aldehyde and by-products are removed from the catchpot 16 by line 17. Gaseous materials are passed via line 18 to separator 19 containing a demisting pad and recycle line 20. Recycle gases are removed by line 21 to line 8 from which a purge through line 22 is pulled to control saturated hydrocarbon content. The remaining and major porportion of the gases can be recycled via line 8 to line 4 into which is fed make-up reactant feeds through lines 2 and 3. The combined total of reactants are fed to the reactor 1. Compressor 26 aids in transporting the recycle gases.

Fresh catalyst solution can be added to the reactor 1 by line 9. The single reactor 1 can of course, be replaced by a plurality of reactors in parallel.

The crude aldehyde product of line 17 can be treated by conventional distillation to separate the various aldehydes and the condensation products. A portion of the crude can be recycled to reactor 1 through line 23 and fed as indicated by broken-line 25 to a point above impeller 6 for the purpose of maintaining the liquid level in reactor 1 if such is required.

The following example serves to illustrate the practice of this invention and not limit it.

EXAMPLE

The reactor employed is a stainless steel cylindrical vessel as characterized in the drawing, having dimension of 13 feet inside diameter and 24 feet height containing a 4 feet diameter, 8 inches inside diameter tubular sparger located immediately below the impeller. The sparger contains a plurality of holes to allow feed of reactants.

The conditions of the reaction using the process design of the drawing are set forth in Tables 1 and 2.

TABLE 1

Contents of Reactor 1

| Component Characterization | Amount |
|---|---|
| Liquid Volume | 42,000 liters |
| Rh, determined as metal* | 275 ppm |
| Triphenyl Phosphine | 7.5 weight % |
| Total butyraldehydes | 35 weight % |
| Trimer | 50 weight % |
| Other higher boiling condensation products | 7.5 weight % |

*The rhodium is supplied as hydridocarbonyltris-(triphenylphosphine)rhodium(I).

TABLE 2

| COMPONENT CHARACTERIZATION | REACTOR FEED | REACTOR EFFLUENT | RECYCLE FLOW | PROPYLENE FEED | SYNTHESIS GAS FEED |
|---|---|---|---|---|---|
| Flow | 26,400 Kg/hour | 26,400 Kg/hour | 20,400 Kg/hour | 3,900 Kg/hour | 2,100 Kg/hour |
| Isobutyraldehyde | 0.3 mole % | 1 mole % | 0.4 mole % | | |
| Normal Butyraldehyde | 1.8 mole % | 8.8 mole % | 2.5 mole % | | |
| $CO_2$ | 1.2 mole % | 1.2 mole % | 1.3 mole % | | .01 mole % |
| Propane | 14.3 mole % | 14.6 mole % | 15.8 mole % | 10 mole % | |
| Propylene | 20.5 mole % | 14.9 mole % | 14.9 mole % | 90 mole % | |
| CO | 9.9 mole % | 4.7 mole % | 6.1 mole % | | 45.5 mole % |
| Methane | 3.7 mole % | 3.9 mole % | 4.3 mole % | | .5 mole % |
| $H_2$ | 48.3 mole % | 50.9 mole % | 54.7 mole % | | 54 mole % |
| REACTOR LINEAR VELOCITY | 0.16 ft./second | | | | |
| Reactor Temperature, °C. | 95 | | | | |
| Line 13 Temp., °C. | | 92 | | | |
| Line 15 Temp., °C. | | 40 | | | |
| Line 8 Temp., °C. | | | 75 | | |
| Line 21 Temp., °C. | | | 40 | | |
| Lines 15 & 17 Temp., °C. | | | 40 | | |

The make-up of product from line 17 is a follows:

| COMPONENT CHARACTERIZATION | CONTENTS OF CRUDE PRODUCT |
|---|---|
| Composition(wt.%) | |
| CO | 0.06 |
| $H_2$ | 0.01 |
| $C_3H_6$ | 4.82 |
| $C_3H_8$ | 4.40 |
| $CO_2$ | 0.39 |
| $CH_4+$ | 0.08 |
| Normal Butyraldehyde | 82.59 |
| Iso Butyraldehyde | 7.14 |
| Aldols | 0.01 |
| EPA | 0.16 |
| $H_2O$ | 0.13 |
| Trimers | 0.20 |
| Diester | 0.01 |
| Diol | 0.01 |
| TPP | Trace |

Essentially the same procedure has been proven to be a most effective technique to produce propionaldehyde from ethylene.

What is claimed is:

1. The continuous process of producing aldehydes by the hydroformylation of alpha-olefins containing 2 to about 5 carbon atoms comprising:

establishing a liquid body of a homogeneous mixture containing olefin, aldehyde products and higher boiling aldehyde condensation products continuously formed therein, a soluble rhodium catalyst complexed with carbon monoxide and a triarylphosphine, and at least ten moles of free triarylphosphine for each mole of rhodium metal;

supplying to the liquid body a gaseous recycle stream comprising hydrogen and the olefin;

supplying make-up quantities of carbon monoxide, hydrogen and olefin to the liquid body;

maintaining the temperature of the liquid body at about 50° C. to about 140° C., the total pressure at less than about 400 psia, the carbon monoxide partial pressure at less than about 50 psia and the hydrogen partial pressure at less than about 200 psia;

removing from said liquid body an amount of vaporous mixture comprising said olefin, hydrogen, vaporized aldehyde product, and an amount of vaporized aldehyde condensation products essentially equal to the rate of their formation in said body whereby the size of said body is maintained at a predetermined value; and recovering aldehyde product and aldehyde condensation product from said vaporous mixture and forming said gaseous recycle stream.

2. The process of claim 1 wherein the alpha-olefin is propylene.

3. The process of claim 1 wherein the gaseous recycle stream comprises hydrogen, the alpha-olefin and carbon monoxide.

4. The process of claim 2 wherein the gaseous recycle stream comprises hydrogen, the alpha-olefin and carbon monoxide.

5. The process of claim 2 wherein the triarylphosphine is triphenylphosphine.

6. The process of claim 1 wherein the total pressure is less than 350 pounds psia.

7. The process of claim 2 wherein the hydrogen to carbon monoxide is at a mole ratio between 3 to 2 and 20 to 1.

8. The process of claim 2 wherein the temperature is from about 60° C. to about 120° C.

9. The process of claim 1 wherein the alpha-olefin is ethylene.

10. The process of claim 1 wherein the alpha-olefin is 1-butene.

* * * * *

UNITED STATES PATENT AND TRADEMARK OFFICE
CERTIFICATE OF CORRECTION

PATENT NO. : 4,247,486
DATED : Jan. 27, 1981
INVENTOR(S) : E.A.V. Brewester and R.L. Pruett It is certified that error appears in the above—identified patent and that said Letters Patent is hereby corrected as shown below:

Column 2 line 8 "*"ppm" should be ---(*"ppm ---.

Column 8, line 17 "referred" should be ---preferred---.

Column 11, line 61 "data" should be ---date---.

Signed and Sealed this

Thirtieth Day of June 1981

[SEAL]

Attest:

RENE D. TEGTMEYER

Attesting Officer     Acting Commissioner of Patents and Trademarks